(12) United States Patent
Ciezobka et al.

(10) Patent No.: US 10,781,680 B2
(45) Date of Patent: Sep. 22, 2020

(54) DETECTION AND QUANTIFICATION OF PROPPANT FOR OPTIMIZED FRACTURE TREATMENT DESIGN IN IN-FILL AND NEW WELLS

(71) Applicant: GAS TECHNOLOGY INSTITUTE, Des Plaines, IL (US)

(72) Inventors: Jordan Ciezobka, Addison, IL (US); Sarah Eisenlord, Libertyville, IL (US); Debotyam Maity, Schaumburg, IL (US)

(73) Assignee: GAS TECHNOLOGY INSTITUTE, Des Plaines, IL (US)

( * ) Notice: Subject to any disclaimer, the term of this patent is extended or adjusted under 35 U.S.C. 154(b) by 160 days.

(21) Appl. No.: 15/892,081

(22) Filed: Feb. 8, 2018

(65) Prior Publication Data
US 2018/0223641 A1    Aug. 9, 2018

Related U.S. Application Data

(60) Provisional application No. 62/456,282, filed on Feb. 8, 2017.

(51) Int. Cl.
| | | |
|---|---|---|
| E21B 43/267 | (2006.01) | |
| G01N 21/29 | (2006.01) | |
| G01N 1/34 | (2006.01) | |
| G01N 15/02 | (2006.01) | |
| E21B 21/06 | (2006.01) | |
| G01N 21/31 | (2006.01) | |
| G01N 21/33 | (2006.01) | |
| G01N 21/35 | (2014.01) | |
| G01N 27/72 | (2006.01) | |
| G01T 1/16 | (2006.01) | |

(Continued)

(52) U.S. Cl.
CPC .......... *E21B 43/267* (2013.01); *E21B 21/065* (2013.01); *G01N 1/34* (2013.01); *G01N 15/0205* (2013.01); *G01N 15/0227* (2013.01); *G01N 15/1475* (2013.01); *G01N 21/29* (2013.01); *G01N 21/33* (2013.01); *G01N 21/35* (2013.01); *G01N 27/72* (2013.01); *G01T 1/1603* (2013.01); *G01N 33/2823* (2013.01); *G01N 2015/1486* (2013.01); *G01N 2015/1493* (2013.01); *G01N 2015/1497* (2013.01); *G01N 2021/3155* (2013.01); *G01N 2201/10* (2013.01)

(58) Field of Classification Search
CPC ...... E21B 43/67; E21B 49/087; E21B 49/006; E21B 21/063; E21B 21/066
See application file for complete search history.

(56) References Cited

U.S. PATENT DOCUMENTS

| | | | |
|---|---|---|---|
| 2,435,843 A | * | 2/1948 | Rand ..................... E21B 49/005 250/255 |
| 5,441,110 A | | 8/1995 | Scott, III |

(Continued)

*Primary Examiner* — Jennifer H Gay
(74) *Attorney, Agent, or Firm* — Pauley Erickson & Swanson

(57) ABSTRACT

A system and method for detecting and quantifying proppant for optimized fracture treatment design in in-fill and new wells. Proppant is isolated from drilling fluids and then analyzed to determine whether a formation within the well has been properly stimulated based on the analysis. Placement of an in-fill well may be based upon the determination of whether the well has been properly stimulated.

18 Claims, 16 Drawing Sheets

(51) Int. Cl.
*G01N 15/14* (2006.01)
*G01N 33/28* (2006.01)

(56) References Cited

U.S. PATENT DOCUMENTS

| | | | | |
|---|---|---|---|---|
| 6,657,752 B1* | 12/2003 | Tseng | | H04N 1/02815 |
| | | | | 358/474 |
| 6,691,780 B2* | 2/2004 | Nguyen | | C09K 8/805 |
| | | | | 166/254.1 |
| 6,715,347 B2* | 4/2004 | Zamfes | | G01N 15/042 |
| | | | | 250/255 |
| 6,725,926 B2* | 4/2004 | Nguyen | | C09K 8/805 |
| | | | | 166/254.1 |
| 7,921,910 B2* | 4/2011 | Wilson | | C09K 8/80 |
| | | | | 166/250.12 |
| 8,354,279 B2* | 1/2013 | Nguyen | | C09K 8/805 |
| | | | | 436/27 |
| 8,701,774 B2* | 4/2014 | Johnson, Sr. | | C09K 8/032 |
| | | | | 166/308.2 |
| 10,281,380 B1* | 5/2019 | Bryant | | G01N 3/12 |
| 2002/0118406 A1* | 8/2002 | Huang | | H04N 1/04 |
| | | | | 358/506 |
| 2003/0196799 A1* | 10/2003 | Nguyen | | C09K 8/805 |
| | | | | 166/250.12 |
| 2003/0196800 A1* | 10/2003 | Nguyen | | C09K 8/805 |
| | | | | 166/254.1 |
| 2004/0129923 A1* | 7/2004 | Nguyen | | C09K 8/805 |
| | | | | 252/301.4 R |
| 2004/0162224 A1* | 8/2004 | Nguyen | | C09K 8/805 |
| | | | | 507/200 |
| 2005/0109087 A1 | 5/2005 | Robb et al. | | |
| 2008/0149329 A1 | 6/2008 | Cooper et al. | | |
| 2008/0210421 A1* | 9/2008 | Wilson | | C09K 8/80 |
| | | | | 166/254.1 |
| 2008/0239334 A1* | 10/2008 | Jasinski | | H04N 1/603 |
| | | | | 358/1.6 |
| 2009/0288820 A1* | 11/2009 | Barron | | B01J 13/02 |
| | | | | 166/249 |
| 2010/0313645 A1* | 12/2010 | Doman | | E21B 21/066 |
| | | | | 73/152.04 |
| 2011/0177984 A1* | 7/2011 | Wilson | | C09K 8/80 |
| | | | | 507/219 |
| 2011/0272156 A1* | 11/2011 | Johnson, Sr. | | C09K 8/032 |
| | | | | 166/280.1 |
| 2012/0264660 A1* | 10/2012 | Nguyen | | C09K 8/805 |
| | | | | 507/203 |
| 2013/0233536 A1* | 9/2013 | Alqam | | G01N 3/00 |
| | | | | 166/250.01 |
| 2014/0000891 A1* | 1/2014 | Mahoney | | C09K 8/805 |
| | | | | 166/280.2 |
| 2014/0014348 A1* | 1/2014 | Mahoney | | C09K 8/805 |
| | | | | 166/308.2 |
| 2014/0182841 A1 | 7/2014 | Lecerf et al. | | |
| 2014/0228258 A1* | 8/2014 | Mahoney | | C09K 8/805 |
| | | | | 507/219 |
| 2014/0332199 A1 | 11/2014 | Gilstad et al. | | |
| 2014/0333754 A1* | 11/2014 | Graves | | E21B 44/00 |
| | | | | 348/85 |
| 2015/0114640 A1* | 4/2015 | Bestaoui-Spurr | | C09K 8/805 |
| | | | | 166/280.2 |
| 2015/0345258 A1* | 12/2015 | Sanborn | | E21B 21/062 |
| | | | | 166/311 |
| 2016/0130499 A1* | 5/2016 | Nguyen | | C09K 8/805 |
| | | | | 166/280.2 |
| 2016/0305237 A1* | 10/2016 | Klemin | | E21B 43/00 |
| 2017/0108428 A1* | 4/2017 | Rowe | | G01N 21/15 |
| 2017/0247995 A1* | 8/2017 | Crews | | E21B 41/0035 |
| 2018/0010429 A1* | 1/2018 | Willberg | | E21B 43/26 |
| 2018/0112478 A1* | 4/2018 | Goloshchapova | | E21B 21/066 |
| 2018/0223641 A1* | 8/2018 | Ciezobka | | E21B 43/267 |
| 2018/0306016 A1* | 10/2018 | Safonov | | C09K 8/60 |
| 2018/0364381 A1* | 12/2018 | Raterman | | G01V 1/308 |

* cited by examiner

FIG. 1
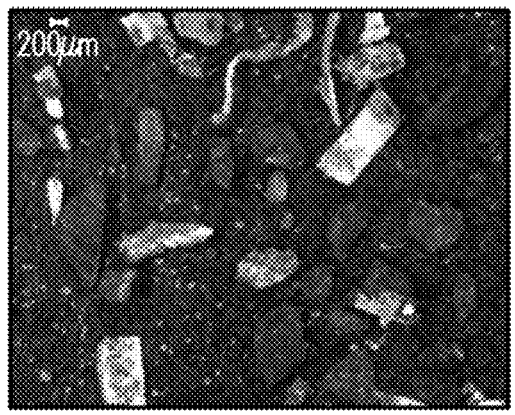 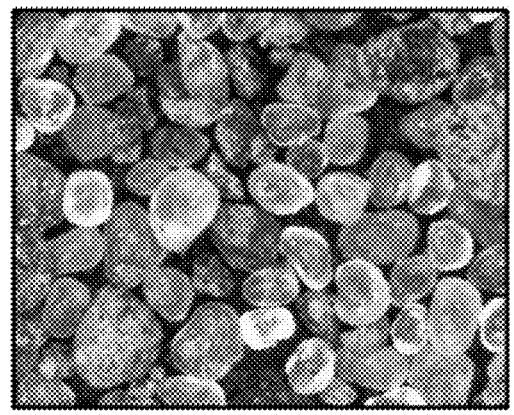
FIG. 2A				FIG. 2B

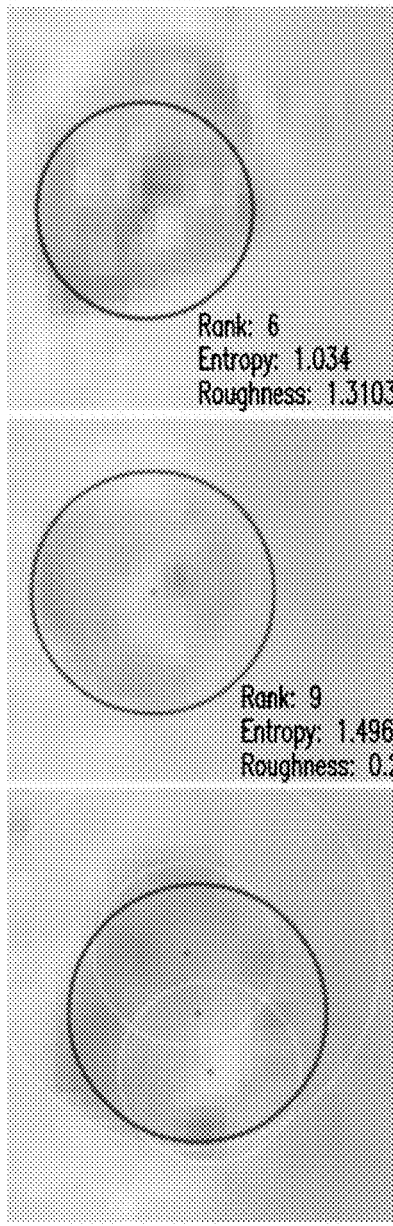
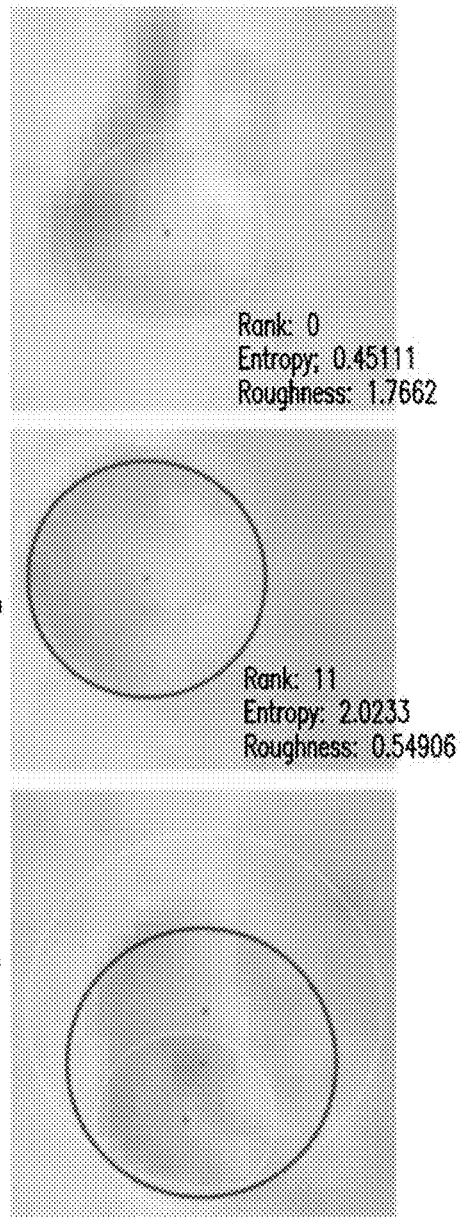
FIG. 6A  
Rank: 6  
Entropy: 1.034  
Roughness: 1.3103
FIG. 6B  
Rank: 0  
Entropy: 0.45111  
Roughness: 1.7662
FIG. 6C  
Rank: 9  
Entropy: 1.4967  
Roughness: 0.24631
FIG. 6D  
Rank: 11  
Entropy: 2.0233  
Roughness: 0.54906
FIG. 6E
FIG. 6F

DETECTION AND QUANTIFICATION OF PROPPANT FOR OPTIMIZED FRACTURE TREATMENT DESIGN IN IN-FILL AND NEW WELLS

CROSS REFERENCE TO RELATED APPLICATION

This application claims the benefit of U.S. Provisional Application Ser. No. 62/456,282, filed 8 Feb. 2017. This application is hereby incorporated by reference herein in its entirety and is made a part hereof, including but not limited to those portions which specifically appear hereinafter.

GOVERNMENT RIGHTS

This invention was made with government support under Contract No. DE-FE0024292 awarded by the U.S. Department of Energy. The government has certain rights in the invention.

BACKGROUND OF THE INVENTION

Field of the Invention

This invention relates generally to a system and method for detecting and quantifying proppant for optimized fracture treatment design in in-fill and new wells.

Discussion of Related Art

During a traditional hydraulic fracturing operation a section of the wellbore is stimulated, or hydraulically fractured. The fracturing fluid travels through the wellbore, then through the open set of perforations and then into the hydrocarbon bearing gas shale, thus creating hydraulic fractures. During drilling of new wells, infill or adjacent, sludge samples can be collected (containing drilling mud, rock cuttings, and previously placed proppant). The ability to quantify proppant in the collected sludge enables the understanding of proppant distribution in the reservoir. This is important to know since it is believed that only propped fractures contribute to significant production.

SUMMARY OF THE INVENTION

The subject invention is a system and method for detection and quantification of proppant for optimized fracture treatment design in in-fill wells and new offset wells. In a preferred embodiment, the method of this invention begins by removing drilling mud, sludge, waste materials and/or even a through-fracture whole core from a reservoir in order to analyze created hydraulic fractures and re-activated natural fractures. The subject method preferably includes isolating solid shale and proppant from an oily sludge matrix of the core. The isolated solid shale and proppant is then analyzed using visual methods and/or computer based analysis in order to collect attribute data of the proppant in order to perform qualitative and quantitative proppant analysis. From the attribute data, a user of the system of this invention will be able to determine which parts of the reservoir have been properly stimulated and which parts of the reservoir have been improperly stimulated and focus additional fracturing to maximize production.

BRIEF DESCRIPTION OF THE DRAWINGS

These and other objects and features of this invention will be better understood from the following detailed description taken in conjunction with the following drawings.

FIG. 1 shows an image of washed sludge including pieces of shale with natural calcite according to one preferred embodiment of the invention.

FIG. 2A shows an image of washed and sieved sludge taken with a stereomicroscope according to one preferred embodiment of the invention.

FIG. 2B shows an image of washed and sieved sludge taken with a stereomicroscope according to one preferred embodiment of the invention.

FIG. 6 shows an image scan of a set of slides showing non-proppant, proppant and re-identified proppant according to one preferred embodiment of the invention.

DESCRIPTION OF PREFERRED EMBODIMENTS

Figure 3:
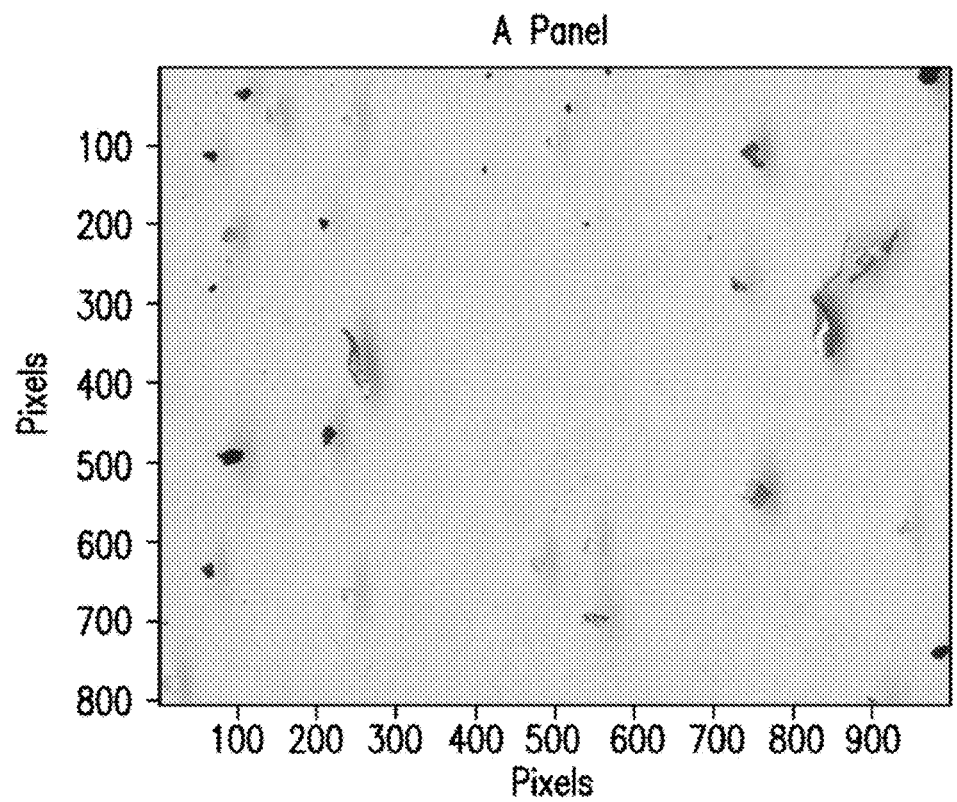
FIG. 3 shows an image scan of material from core barrels of an infill well according to one preferred embodiment of the invention.

This invention relates generally to a system and method for detecting and quantifying proppant for optimized fracture treatment design in in-fill and offset new wells.

Subsurface Proppant Detection

A Hydraulic Fracturing Test Site (HFTS) was used for a series of trials to develop the subject methods. At the HFTS through-fracture whole core are recovered in order to capture created hydraulic fractures and re-activated natural fractures. Since proppant was pumped in the hydraulic fracturing slurry in the offset wells, it was anticipated that proppant would be found in the collected whole core as well. As such, once the core was taken out of the core barrels at the lab, the sludge surrounding the core was recovered and stored. A majority of the sludge was located on the outside of the core, and in the core barrel itself. The sludge is known to contain drilling mud residue, rock cuttings, and proppant. Sludge was collected from the individual fractures in core while performing core description. In either case, the sludge collected from the core barrel and from the created fractures should contain the same materials.

The ability to quantify proppant in the collected sludge enables the understanding of proppant distribution in the reservoir. This is important to know since it is believed that only propped fractures contribute to significant production.

This application discusses the methods used to wash and analyze the sludge recovered from the core in order to quantify the proppant concentration and size in the cored well. Utilizing this knowledge, a new method for optimizing in-fill well fracture design and spacing is developed. Furthermore, this application applies this information to new field well drilling and fracturing programs.

Clean Sludge and Detect in Lab

Two methods were successful in isolating the solid shale and proppant pieces from the oily sludge matrix. A method for separating the shale shards from the proppant has proven more difficult, however, once cleaned, sieved and dried, the proppant is distinguishable from the shale with image recognition software as discussed below.

Initially three solvents were tested for dissolving the oily sludge matrix: hexane, methanol, and acetone. Approximately 1 gram of sludge material was mixed with 30 mL of either hexane+methanol, hexane+acetone, acetone alone, or methanol alone. Mixture was stirred manually and then rinsed three times, the first with more solvent, and then with clean water. The hexane+methanol proved to be most effective in removing the oily matrix.

The second method tested has considerably less cost and environmental impact as it does not use hazardous materials, but hand soap and laundry softener instead. Approximately 1 g of sludge was mixed with 0.5 mL hand soap and 0.25 mL laundry softener, mixed manually, and rinsed three times with clean water.

After the third rinse, or when the rinse water runs clear, the resulting material (shards of shale, aluminum shavings, and proppant pieces) are wet sieved through stacked screens, for example 20 mesh and 120 mesh screens. The screens are then dried in a ventilated oven, for example at 75° C. for 25 min and the material on top of the 120 mesh screen is collected for visualization.

Many of the sludge samples are greater than 1 gram in size, ranging up to 145 grams when wet, or more. The clean and dried size fraction between the 20 and 120 mesh ranges between 1 and 15 grams. A sub-sampling regimen was developed that provides proppant concentrations and size distributions representative of the whole sample without having to image it in its entirety.

A riffler may be used to split the clean and dry 20-120 mesh size fraction in half without biasing particle weight or size. Once split, half of the sample is returned to the sample jar and the other half is split again through the device. This process is repeated until the final sample weight is approximately 0.25 grams. This is a preferable sample size for good distribution and separation for imaging, discussed in the following section. This process is repeated two more times for a total of three sub samples per sample. The starting weight of the 20-120 fraction is recorded as well as the weights of each sub sample for calculating total proppant concentration.

Cleaning, drying and sieving of the sludge samples also allows for the detection of natural fractures in the deep subsurface through the identification of calcite pieces or cement fill, as seen on the larger size fragments in FIG. 2. Pieces of calcite are also identifiable at the smaller 20-120 mesh size scale, and distinguishable from the proppant pieces by their opacity and classically shaper edges as observed in FIG. 5. Calcite is also identifiable as white crystals on the shale.

Manual Proppant Analysis

Several methods were tested for visualization and identification of proppant. First, a Zeiss Stemi SV11 stereomicroscope with Pax-it. The software yielded high quality, sharp images, however the imaging system was considerably limited in its range of view for processing large samples. Examples of images of washed and sieved sludge taken with this setup are seen in FIGS. 2A and 2B.

Next, a Cannon EOS 20D camera with a Macro lens was positioned above a small flat dish containing the cleaned and washed material. Multiple backgrounds were tested (including printed black, matte black, and white paper) as well as multiple light sources (including white light, blue LED light, black light) to determine visibility properties of the various proppant. It was determined that the field of view in focus was still too small and unreliably in focus for processing large samples. The various light sources did not improve the ability to discern proppant from shale or aluminum pieces. At the same time, shadow and reflections were causing significant challenges in automated object detection.

Another method to image the washed and sieved sludge sample is to use a high-resolution flatbed scanner, for example, an Epson Expression 11000XL graphics arts scanner. The dried samples are spread out on a transparent sheet or glass and then another sheet or glass is overlaid on top. The prepared sample slides are then scanned at a high resolution to generate images for further analysis. Another alternative is to use reflective scanning instead of transparency scanning. Here various background colors and various light sources can be used. Common combinations could be white light with a white or a black background. The use of the scanner allows for reduced optical distortions, controlled lighting and image quality parameters as well as improved image SNR for automated proppant detection and analysis workflow. Higher resolutions of up to 2400 dpi allow discrimination and classification of extremely small particles (~200 mesh).

Qualitative and Quantitative Proppant Analysis

Data on the presence, quantity, and size of proppant is collected for qualitative and quantitative information. Qualitatively, individual pieces of normal, colored, or otherwise tagged proppant can be detected in core sludge or drilling mud when used in specific fracture stages to identify what stage certain fractures originated in. Quantitatively, the ability to count and size proppant yields information on how much proppant is washed out of fractures during the drilling process and how many fractures the new well traverses.

Automatic Proppant Analysis—Reflective Scanning

Based on the slides/images, etc. from scanner, camera or microscope, an image processing workflow is used to detect the proppant from each of the slides. It is to be noted that a white background is used for the detection workflow but a black or any other colored background can also be used. With the white background, translucent proppant particles are very bright and tend to merge with the background compared with shale particles, some naturally occurring calcite pieces, and aluminum shavings from the core barrel (since these collections are from cores obtained from an infill well). The workflow involves careful selection of pre-processing filters to enhance the features of the proppant in relation to the features of other particles within the slides such as shale/rock pieces, hydrocarbon rich particles, mud particles (from drilling), etc. Various particle attributes are computed and they are then ranked based on the behavior of these attributes. The ranking can be done using decision trees, multi-criteria decision systems, machine learning, etc. Significant attributes used with reflective imaging and white/black background are as follows:

1. Mean darkness of object compared to background. This attribute measures how dark the detected object is compared to the background spectra (which can be colored or white). Various statistical measures such as quantile, mean, standard deviation, etc. from the object's Grayscale spectrum.

2. White ratio within object (reflection). This attribute is computed using a cut-off used to bin the object data into light and dark sections. It can be calculated as the fraction of pixels falling within the lighter sections compared to the total pixel size of the object in question. This is similar to translucence attribute (discussed later) for translucent particle using transparency imaging.

3. Shape of object (object roundness). Proppant particles tend to be roundish in shape with relatively smooth edges [particularly at 40-70 mesh size range]. This is also true for smaller particles but they may also contain edge effects (proppant crushing). However, since smaller proppant particles have more edges and imperfections, the classification has to be adequately modified to cater for variation in particle size. The peaks of the Hough transform accumulator array are used as a measure for particle roundness. Another method for calculating the shape is by extracting data along various azimuths '$\theta$' and calculating the range of high/low values within these azimuthal lines and their variance with '$\theta$'.

4. Entropy of object (texture). Entropy is a statistical measure of randomness of the object within an image and is an indicator of texture of said object. One way for calculating this measure is to use the histogram of data from the object image. We calculate this attribute by extracting data along various azimuths '$\theta$' and calculating the gradient for these azimuthal lines. For each gradient distribution, randomness can be computed using any measure designed to see how the gradient varies linearly. An example would be the second derivative of the data along each azimuthal line.

5. Object color (RGB range, ratios and skewness of spectra). This attribute can be used to detect objects that are colored which could be indicative of colored proppant or an indication of natural calcite, shale particles etc., depending on their observed color spectra. If tagged proppant such as colored proppant is used, this can be used to discriminate between proppant particles of varying colors. With transparency imaging (as discussed later), this attribute can be further used for a blue hue detection which is critical is classifying proppant/natural calcite particles from shale, etc.

6. Extremity dark/white band ratio of object from greyscale image. This provides a measure of how light or dark the particle is close to its outer edges. This acts as another measure of particle roundness. For objects that are rough around the edges or not circular, the outer periphery is tested to see how the white ratio varies with azimuthal angle '$\theta$'. For objects that have rough edges, there is a tendency for the search space to show up significant zones of light sections influenced by the image background. These zones generally showing up as continuous white band zones are another indicator of rough objects, which may have been misclassified proppant. Light bands are indicative of either proppant or aluminum particles. Depending on the background and light source used, it may be necessary to pre-process the object such as inverting greyscale image, etc., to apply this attribute.

Figure 4:
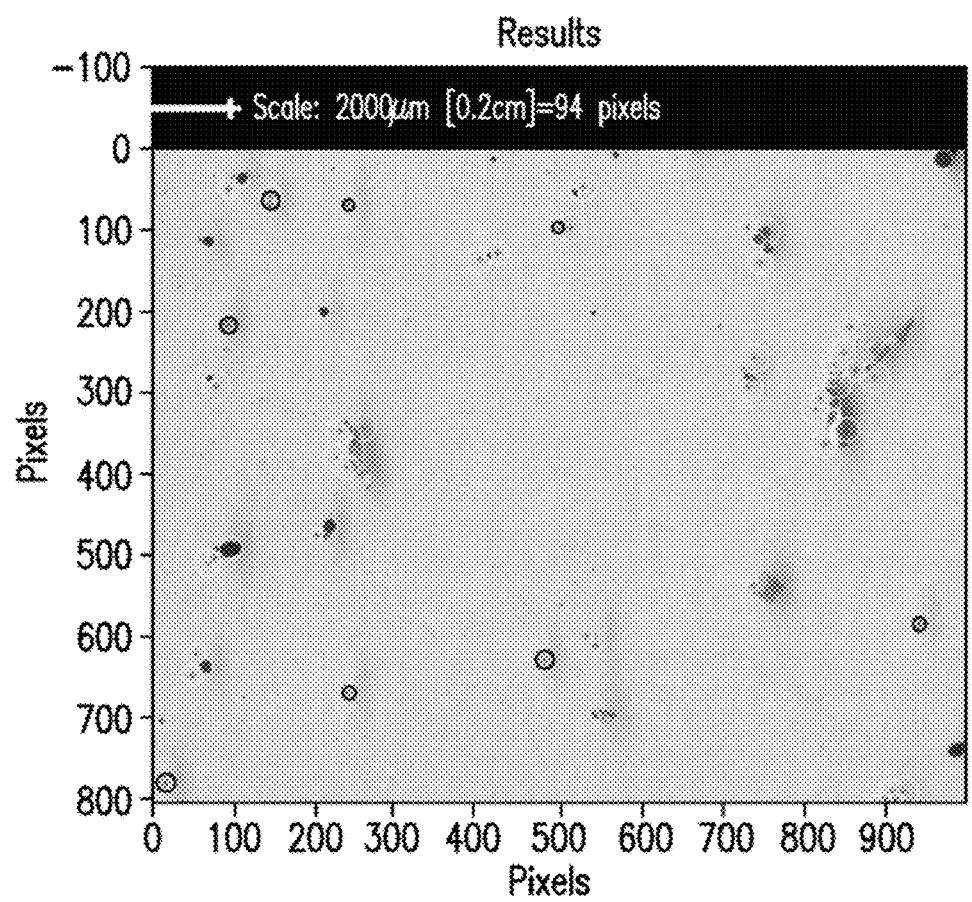
FIG. 4 shows an image scan of material from FIG. 3 including detections to provide a likely object subset from all identified objects according to one preferred embodiment of the invention.

Other attributes can be added of the list can be modified to optimize results based on observations. FIG. 4 shows a sample processed through this workflow.

The pre-processing steps can also involve trimming the contrast levels to darken the particles, using edge detection and edge enhancement filters, etc. The detection routine utilizes a modified Hough transform to look for circular objects within the image. Other methods such as Radon transforms; curvelet transforms; simulated annealing; genetic algorithms; randomized detection algorithms; etc. can also be used for the preliminary detection of objects of interest. Once all objects are detected, a channel (R, G or B) is selected and the distribution of channel values for each object is determined (for example, the Red channel). Alternatively, a measure based on multiple channels such as mean or sum may be used. Based on the nature of this distribution as well as the distribution of the same channel in the original image, detections are pruned to provide us with the most likely object subset from all identified objects, as shown in FIG. 4, which can then be further analyzed for classification. Note that selected probable proppant are enclosed in a black circle while other objects are enclosed in a white circle. Alternately, natural calcite particles can also be classified provided adequate discrimination can be made between the calcite particles on one hand and proppant particles or shale/aluminum pieces on the other. Presence of calcite would indicate that a cemented natural fracture was encountered.

Figure 5:
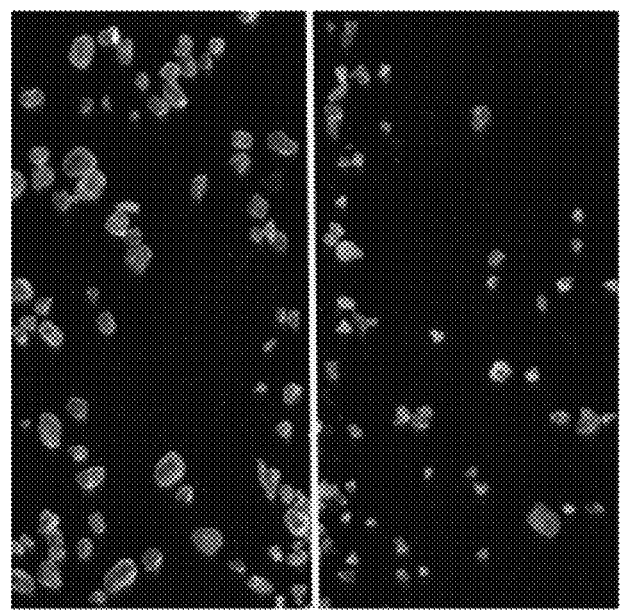
FIG. 5 shows an image scan of proppant on the left and natural calcite on the right according to one preferred embodiment of the invention.

The workflow provides various necessary estimates that can be further used to quantify confidence in detections and probability of a detected object being naturally occurring calcite (i.e., not proppant). FIG. 5 shows a comparison between the two to highlight the challenge in classifying these two types from overall detections. In order to classify these separately, the workflow provides estimates of both by classifying roughness and texture or particles as discussed earlier. FIG. 6 shows example of particles that are probably natural calcite (slides a & b) and those that are proppant (slides c & d) to highlight the differences in the relevant attributes. Some post processing re-identification can also be a part of the workflow as highlighted in FIG. 6, slides e & f. Notice that for proppant particles, entropy is generally high and roughness is generally low as discussed earlier.

The workflow also has an AI (artificial intelligence) mode that can be followed up with a manual QC step. The aim is to isolate and tag the actual proppant and non-proppant objects that the workflow detects and to use the same attributes discussed earlier for a learning algorithm based on artificial neural nets (ANN). The ANN identifies objects as either "proppant" or "non-proppant" based on the trained model. The model once trained can be applied on other datasets from a single trained instance. Alternatively, multiple trained models can be derived and their ensemble can be used for identification when being applied to other datasets.

Figure 7A:
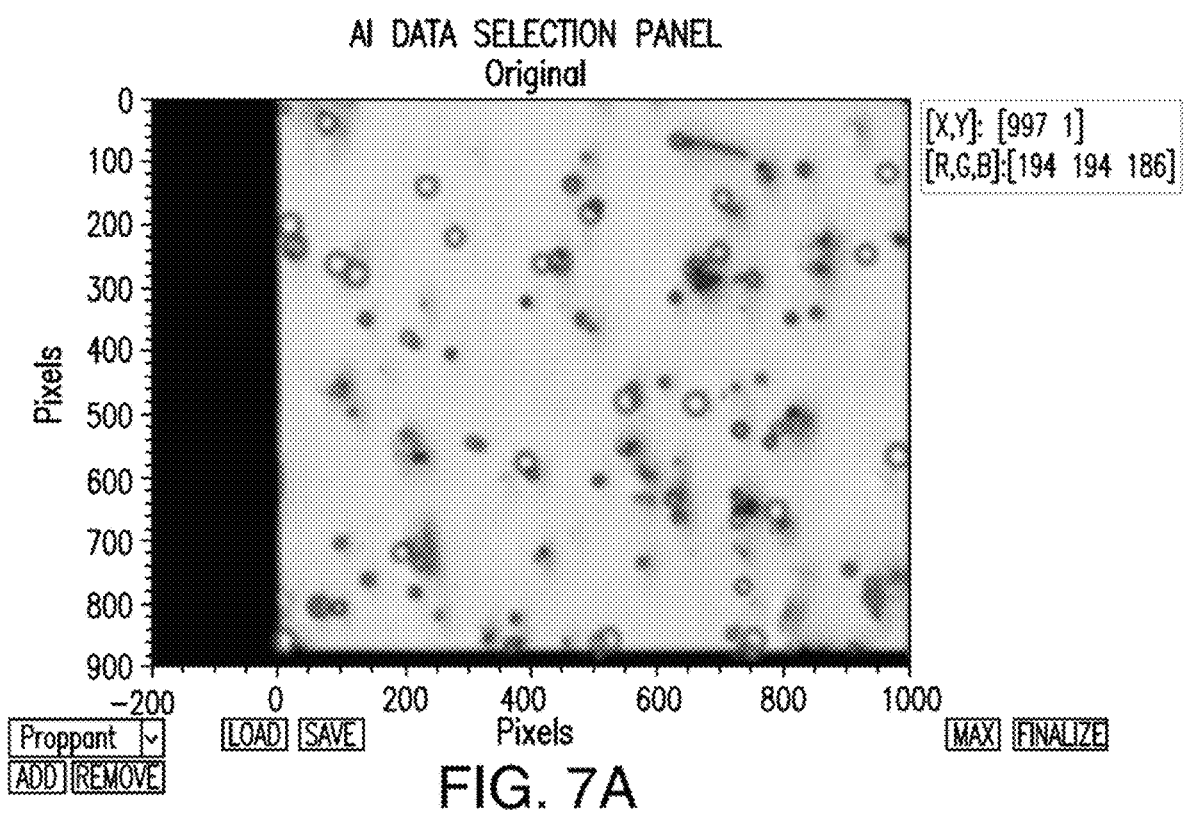
FIG. 7A shows an image scan of an AI based detection workflow according to one preferred embodiment of the invention.
Figure 7B:
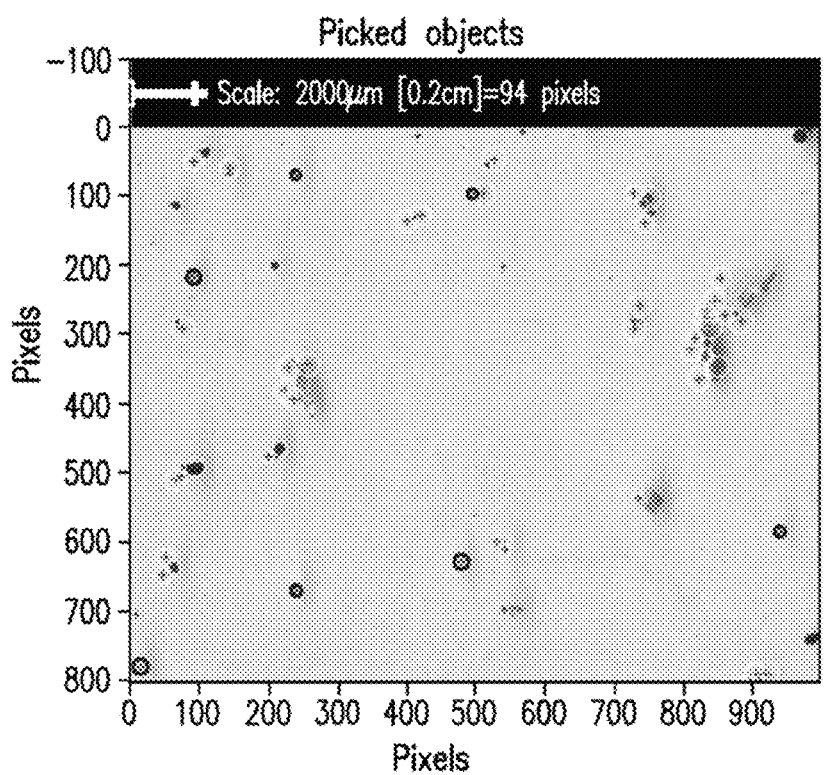
FIG. 7B shows an image scan of an AI based detection workflow according to one preferred embodiment of the invention.

FIG. 7A shows a sample dataset divided into "proppant" and "non-proppant" objects for AI implementation. FIG. 7B shows results of applying the trained model on another dataset. AI models developed during manual QC intervention can help provide independent and quantifiable estimate of confidence for selections made using this workflow. Also, note that an alternative classification could involve classification of both proppant as well as natural cement material such as calcite from shale/rocks, etc.

Figure 8:
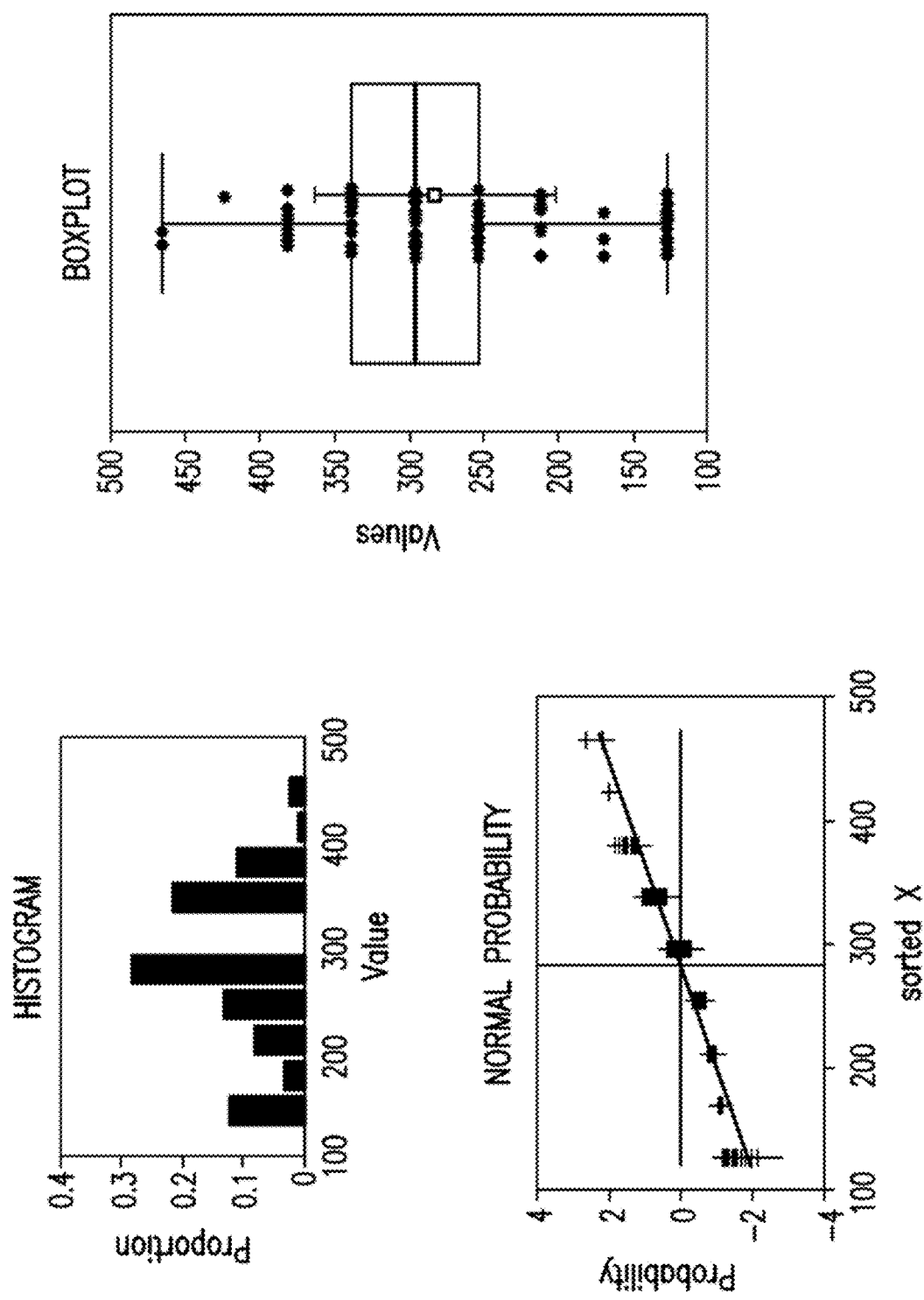
FIG. 8 shows charts of size distribution of identified proppant according to one preferred embodiment of the invention.

FIG. 8 shows the particle size distribution of the objects identified from the image processing workflow. Since the proppant used was 40/70 mesh, we expect most of the proppant to range from 210 to 420 microns and that is what we see from the distributions. We do note that a larger population of fines is detected which are either crushed proppant or misclassification errors due to resolution limits of the slides being processed.

Automatic Proppant Analysis—Transparency Scanning

Figure 9:
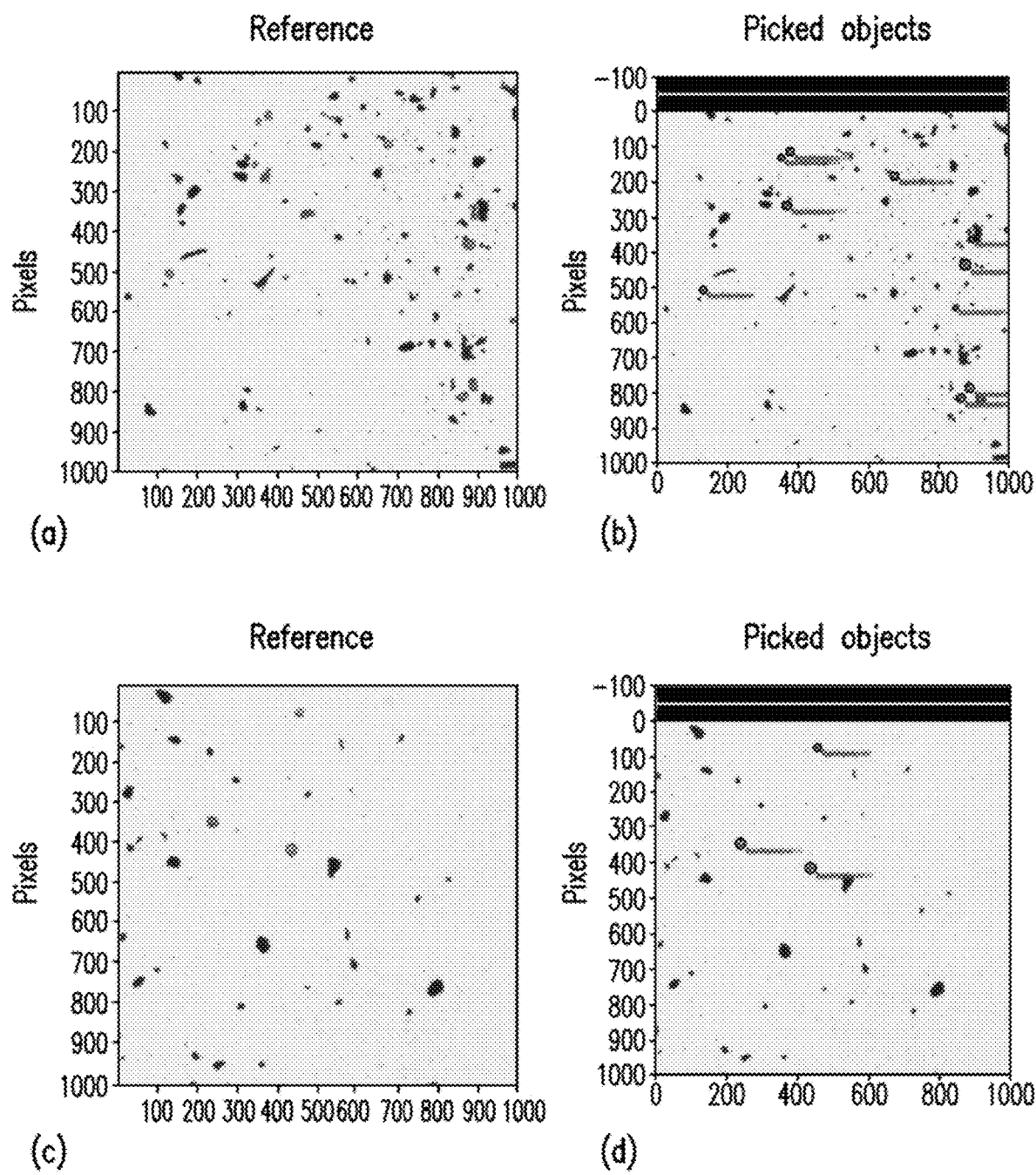
FIG. 9 shows image scan of a set of slides showing image and identified proppant particles according to one preferred embodiment of the invention.
Figure 10:
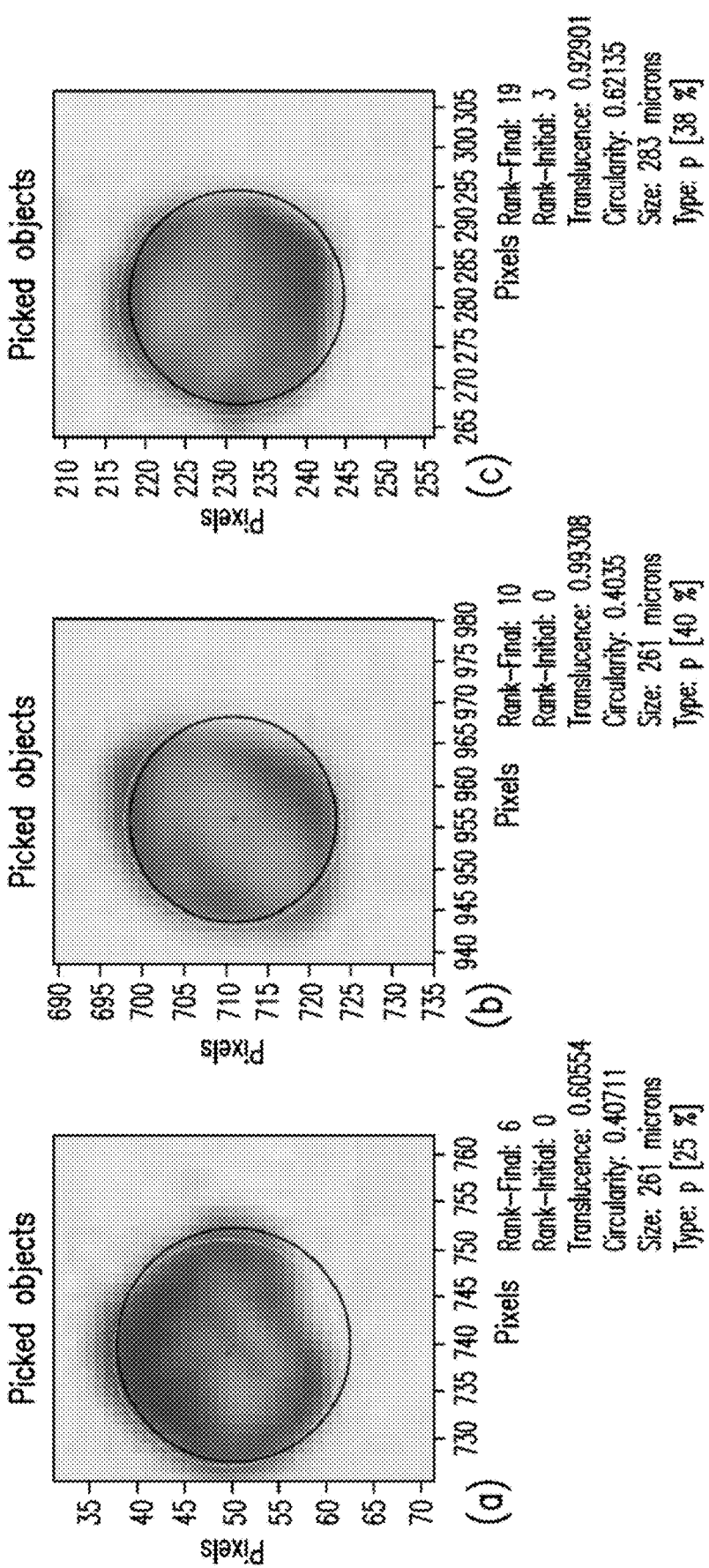
FIG. 10 shows image scans of particles having attributes of hue, translucence and roundness, respectively, according to one preferred embodiment of the invention.

A modified methodology has been devised which makes it easier for proppant detection by removing the textural features of shale and aluminum particles and enhancing the translucence of proppant and/or calcite particles. This method involves using a transparency scan where the behavior of particles in question towards white or blue light is utilized to detect proppant/sand particles. While the workflow is similar to what has been shared for white background, the attributes and their use changes significantly. In addition, while some attributes such as entropy are not used with this approach, new attributes have been defined to make use of the distinct behavior of translucent proppant and calcite particles. FIG. 9 shows an example scan section and identified particles based on the modified workflow.

The workflow as described is usable for sand being used as proppant and other particles (such as ceramic proppants) cannot be identified using this methodology since they do not transmit light in any fashion. At the same time, since these proppant particles are engineered, they have a very smooth finish and are highly resistant to proppant crushing. Therefore, we can use attributes such as roughness and roundness as well as darkness, etc. to discriminate between such engineered proppant particles and naturally occurring calcite, shale, etc. Such a classification workflow is not discussed but may be designed using the same approach that we have described for naturally occurring sand particles used as proppant. Moreover, with tagged proppant such as those that are radioactive, other energy sources can be used instead of optical imaging as a way of detecting them wither in lab or in the field. For sand, we define a few modified/additional attributes to help with classification using transparency imaging. Newly defined attributes are as follows:

1. Color Hue: This parameter is computed using the color spectrum of the identified object after removing a portion of the outer boundary elements. This is used to obtain the degree of bluish or reddish hue in the identified object. For true proppant/calcite particles, the images generally have high bluish hue and very low reddish hue. This is because proppant particles tend to transmit more of the blue spectrum due to absorption of some of the other frequencies within white light. Since absorption is also influenced by particle size, larger particles tend to be darker (more absorption) and vice versa. Some of the aluminum and shale tends to show a reddish hue close to their outer edges that makes it necessary to design a filter based on the reddish hue as well. The size dependence of hue has to be considered when using this attribute for classification. Note that for standard reflective imaging using white light, we expect the proppant/calcite particles to be lightly colored, mostly white or light shades of yellow/red, etc. However, colored resin coated proppant can be relatively dark in color. In case of colored proppant, the presence of dominant color within the spectrum that is not too dark can be used as an identifier for proppant particles or colored proppant particles if they are deliberately introduced for diagnostics. With regular reflective imaging, aluminum particles can also show a blue hue depending on the curvature of the particles and shadow/reflection artifacts. To isolate such objects, other attributes may have to be considered in conjunction as well.

2. Darkness: extremely dark objects are removed as potential shale/aluminum particles. These particles do not transmit light and therefore are very dark under transparency scanning. However, they may show reddish or yellowish hue at the outer edges sometimes due to edge effects. These two attributes when used together can be a good classifier for such particles.

3. Translucence: Sand particles are expected to be translucent when imaged under transparency. This is reflected in light colored bands within the identified objects. These bands are a function of particle size, orientation, degree of clutter or cleanness, and the kind of mineralization (crystal structure) within said particles. The parameter is computed by identifying the relative size of the tail end of the monochromatic spectrum. For regular imaging, proppant particles are expected to be translucent when imaged under white light with a solid background. With regular reflective imaging, translucence over significant portions of identified particles can be indicative of aluminum. This is particularly true if the light band shows significant high values (magnitude of tail section of the monochromatic spectrum). A cut-off used to bin the object data into light and dark sections. It can be calculated as the fraction of pixels falling within the lighter sections compared to the total pixel size of the object in question.

4. Size: Smaller sized particles are generally hard to characterize and therefore if the particle is too small, it is not characterized as proppant. Particle size is identified using either the method used for object detection or by checking the variations in spectrum along various azimuths 'θ' for the identified object compared to its surrounding space.

5. Shape: We select a larger radius based on the identified object size and an edge detection algorithm, which involves use of a filter such as "Sobel" operator, "Prewitt" operator or "Canny" edge detector, etc. Canny detector is the preferred option due to lower false positives. Once the edge highlight is available, the Hough transform algorithm is run to re-compute object center, radius and accumulator array magnitude. If significant difference is not observed between the earlier computed object location and size compared with the secondary values as computed, the probability of the object being an imaging artifact such as shadow etc. is reduced.

We use a combination of parameters to discriminate between potential proppant and calcite particles as well as other objects within the image. In one possible embodiment, we design the workflow involving a ranking scheme such that proppant particles are highly ranked while calcite particles are lower ranked. For the most part, we have been able to get good discrimination between potential proppant and calcite particles. The accuracy is much higher with larger sized particles in terms of both detection as well as discrimination between proppant and calcite, but this is largely a result of a limited scanner resolution. In general, machine learning or Artificial Intelligence (AI) methods are more accurate since they are data driven and can be computationally inexpensive without the need for human intervention. Both approaches may require QC process to eliminate outliers.

Figure 11:
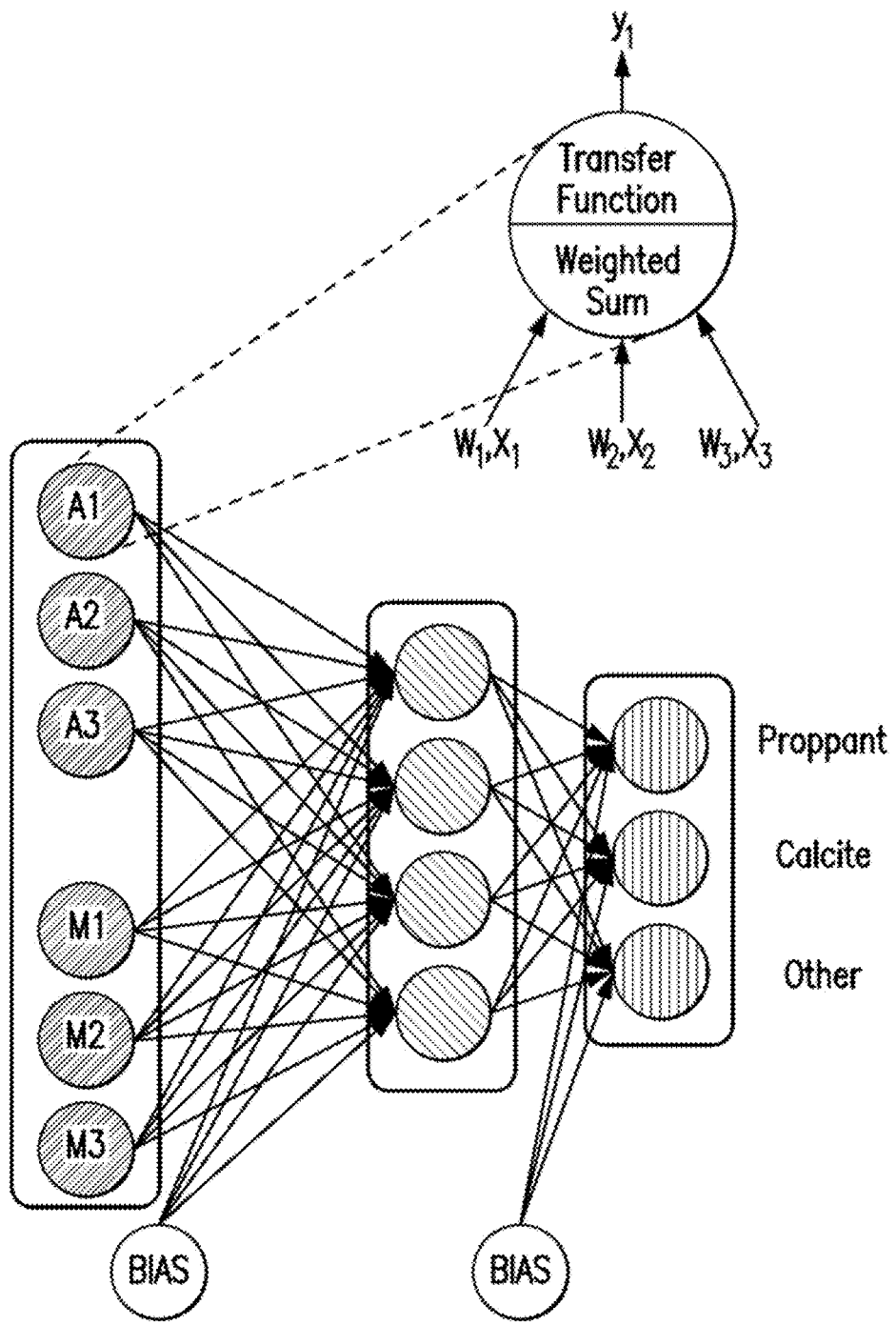
FIG. 11 shows a schematic of a supervised ANN network according to one preferred embodiment of the invention.

We may use an AI based classifier for this problem as well. In this approach, we use either a supervised or an unsupervised method. For a supervised approach such as a supervised artificial neural network (ANN), a training dataset which includes all classes of interest ([proppant and non-proppant] or [proppant, calcite and others]) are identified and labeled. The supervised learning scheme maps the training input data, which includes all of the evaluated attributes, or other meta-attributes, which are a combination of various primary attributes as defined earlier onto an output classification map. FIG. 11 shows a schematic of a supervised ANN network for this problem.

The output defines the classes of interest as per the classifier design. Various types of supervised and unsupervised learning classifiers are available that can be used for this step. Examples include ANN, backpropagation, decision tree, fuzzy decision systems, etc. to name a few. With network designs, selections are made with respect to various design features which can be useful in getting better results without impacting network variance or bias adversely.

Figure 12:
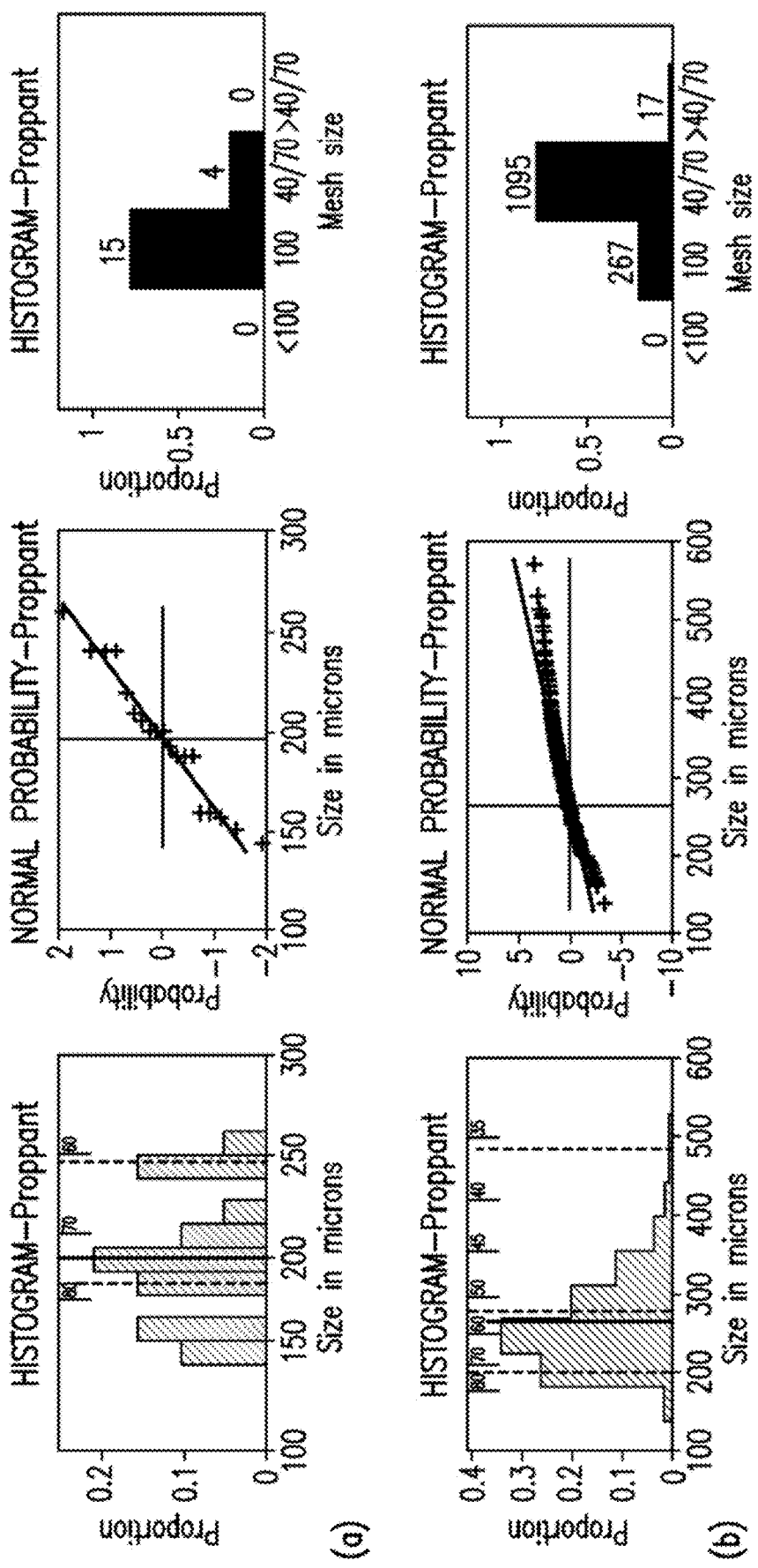
FIG. 12 shows charts of size distribution of identified proppant highlighting a section with no proppant and a section with significant proppant according to one preferred embodiment of the invention.

With the modified workflow using transparency imaging, both type "I" and type "II" errors have been significantly reduced thanks to reduced tendency of the workflow to pick shale or aluminum particles as possible proppant or calcite. Based on the analysis, proppant distribution can be identified for entire sections of the lateral by analyzing the subsamples. There are clear differences between sections with significant proppant and sections without the same. As an example, FIG. 12 shows proppant distribution identified at two different sections of the lateral. We can clearly notice significant proppant population for the latter while the first one has low proppant count (probably statistical error).

When comparing transparency with regular imaging, mineral cement particles can be dark under regular imaging. Their crystalline structure has more irregularities including impurities. This can cause reduced transparency for these particles. However, they still have hue artifact observed with proppant particles under transparency imaging. Using both these imaging methods together, better discrimination occurs between mineral cements naturally occurring in rocks and proppant particles pumped during hydraulic fracturing. This would involve simultaneous imaging of particles using both reflective and transparency imaging and comparing the two sets for same objects from both sets of images obtained.

Once the identified objects have been classified as proppant or otherwise, they can then be used to estimate the relative particle size distribution within the imaged sample. This involves transforming the size information of all detected particles from pixels to microns. Since image resolution is known beforehand, this may be accomplished using the following transformation:

$$Rm = Rp * 25400/dpi$$

Where Rm is the size of particle in microns, Rp is the Radius of object in pixels and dpi is the resolution of the image being processed. Once the sizes have been transformed into microns, they can be further characterized into mesh sizes of interest based on the sizes identified. This is useful since proppant size classification used within the oil and gas industry is by mesh size. The mapping from microns to mesh dimensions is within expected limits of accuracy, which is inherent with any size distribution based on physical mesh screens. Based on desired size distributions that were pumped into the rock formation during original hydraulic fracturing operations, mesh sizes of interest can be identified and analyzed. Furthermore, the distributions that are essentially object counts can be scaled based on some reference to get proppant concentration. This is because the size fractions identified are representative of the sub-sample associated with the scanned image and needs to be scaled to allow comparative analysis. An example reference could be the total weight of the sample tested every foot of well. There is an inherent assumption here that the sub-sample is a true representation of the original sample extracted from the core/drilling mud return, etc. The concentrations can then be compared across the wellbore and can be used for generating proppant or other particle logs. While the proposed detection/l discrimination technique is quite robust, errors in picks, especially for smaller particle size fractions [100 mesh] can occur. In order to tide over this issue and get relatively accurate results in terms of particle counts and size distributions, a comprehensive QC procedure can also be used. The process is broadly outlined as follows:

1. Complete automated detection and classification of objects within the imaged portion of the original sample image.

2. Select image sub-section for QC. Selections based on presence or absence of identified objects. Individually check each identified object within each sub-section.

3. Based on identified misclassification or missed objects, make necessary changes including addition or removal of objects as proppant or calcite or might also include correcting misclassification of proppant or calcite particles.

4. Based on corrections, the relative distribution of various size fractions of both proppant and calcite particles for particular sub-section being quality controlled is adjusted.

5. For all other sub-sections for that sample, adjust the size fractions based on the adjustments made in the quality-controlled sub-section. This involves taking into account the adjustment fractions from the QC process as well as the overall object count within each sub-section for update. The correction is defined as follows:

$$CP_{i,j} = \frac{P_{i,j}^{final}}{P_{i,j}^{initial}} \ \& \ P_{k,j}^{final} = \left[\frac{n_k}{n_i}\right] \times CP_{i,j} \times P_{k,j}^{initial}$$

Note that CP indicates the correction for proppant for a particular scan sub-section, 'i' for a particular size fraction 'j'. 'P' represents the total count of proppant particles for particular scan section as well as size fraction. It is evaluated as either the final count (after QC) or the initial count (prior to QC). Index 'k' represents another sub-section where the correction is to be applied. Parameter 'n' indicates the total particle density (identified objects) for particular scan section in question. Note that the same correction is also applied to the identified natural calcite distributions as well.

6. Based on the updated size fractions from each scan sub-section upon application of corrections, the final size fractions for the entire image is updated to give the post QC size distributions.

Apart from QC process described here, an additional step involving blind comparison with microscopically imaged samples or using other imaging methods can be conducted to validate the results.

Figure 13:
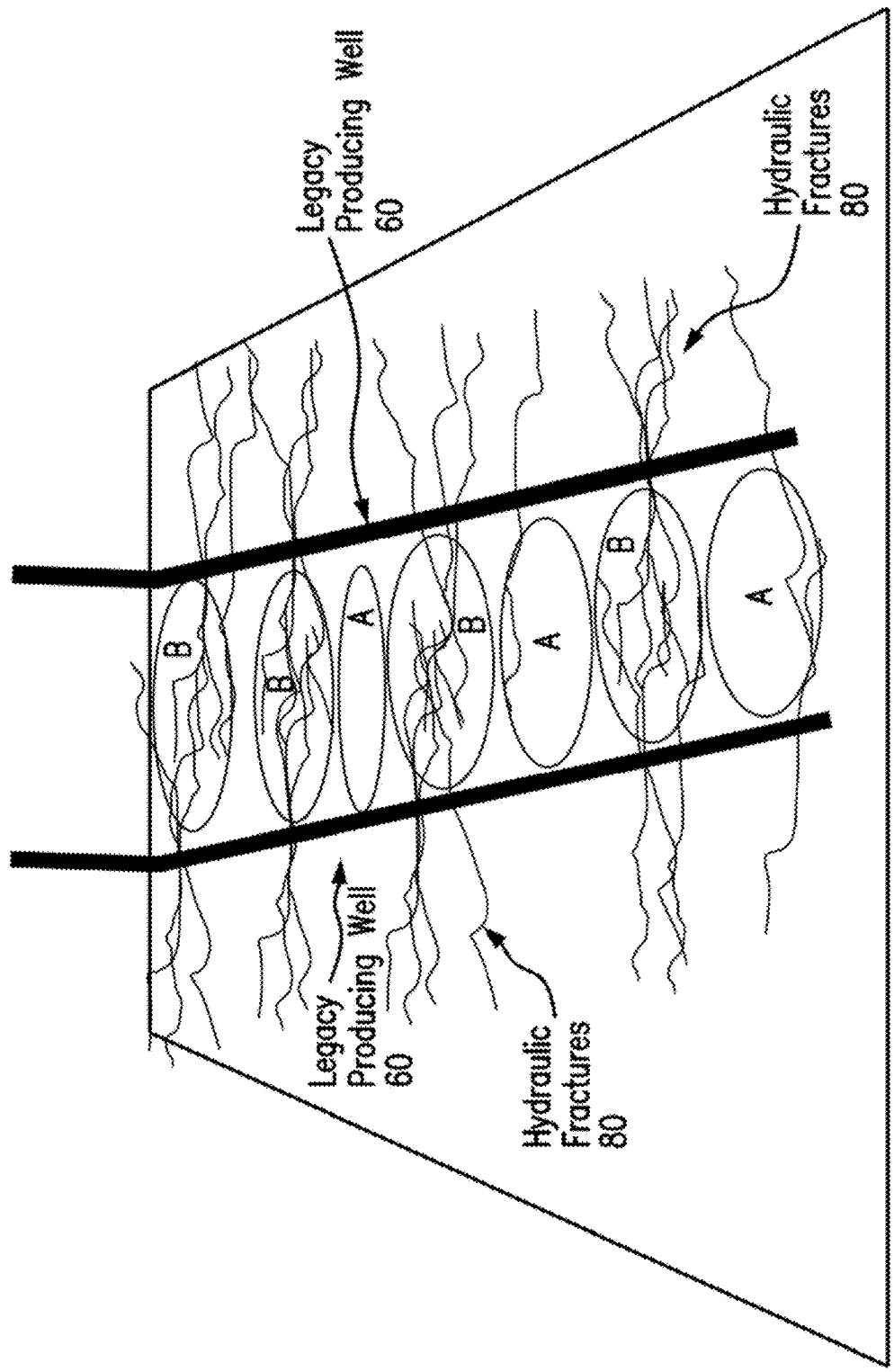
FIG. 13 shows a schematic of two parallel horizontal wells and a stimulated reservoir according to one preferred embodiment of the invention.

In-Fill Well Hydraulic Fracture Optimization Utilizing Known Sub-Subsurface Proppant Distribution Hydrocarbon production from tight rock resources (shale, tight sandstones, etc.) requires permeability enhancement for economic oil and gas volumes to be produced. The most commonly utilized method of permeability enhancement is hydraulic fracturing stimulation and the addition of proppant to hold open the created fractures. During field development, many horizontal wells are drilled in parallel at a desired well spacing, which typically ranges from 500 feet to 1000 feet. Production of oil and gas from the tight rock reservoir is mainly facilitated through the created hydraulic fractures, channeling the hydrocarbons to the wellbore and then up to the surface. FIG. 13 schematically shows two parallel horizontal wells 60 that have been fracture stimulated. In this figure, there are areas of the reservoir between the two producing wells with hydraulic fractures 80 emanating from either or both wells (Red shaded regions denoted B), and there are areas of the reservoir with few or no fractures (blue shaded regions denoted A). Since the reservoir requires stimulation to produce oil and gas, the unstimulated areas will be virtually unproductive during the life of the well. For this reason, an in-fill well is typically drilled to recover stranded reserves, which were left behind due to inadequate stimulation.

Figure 14:
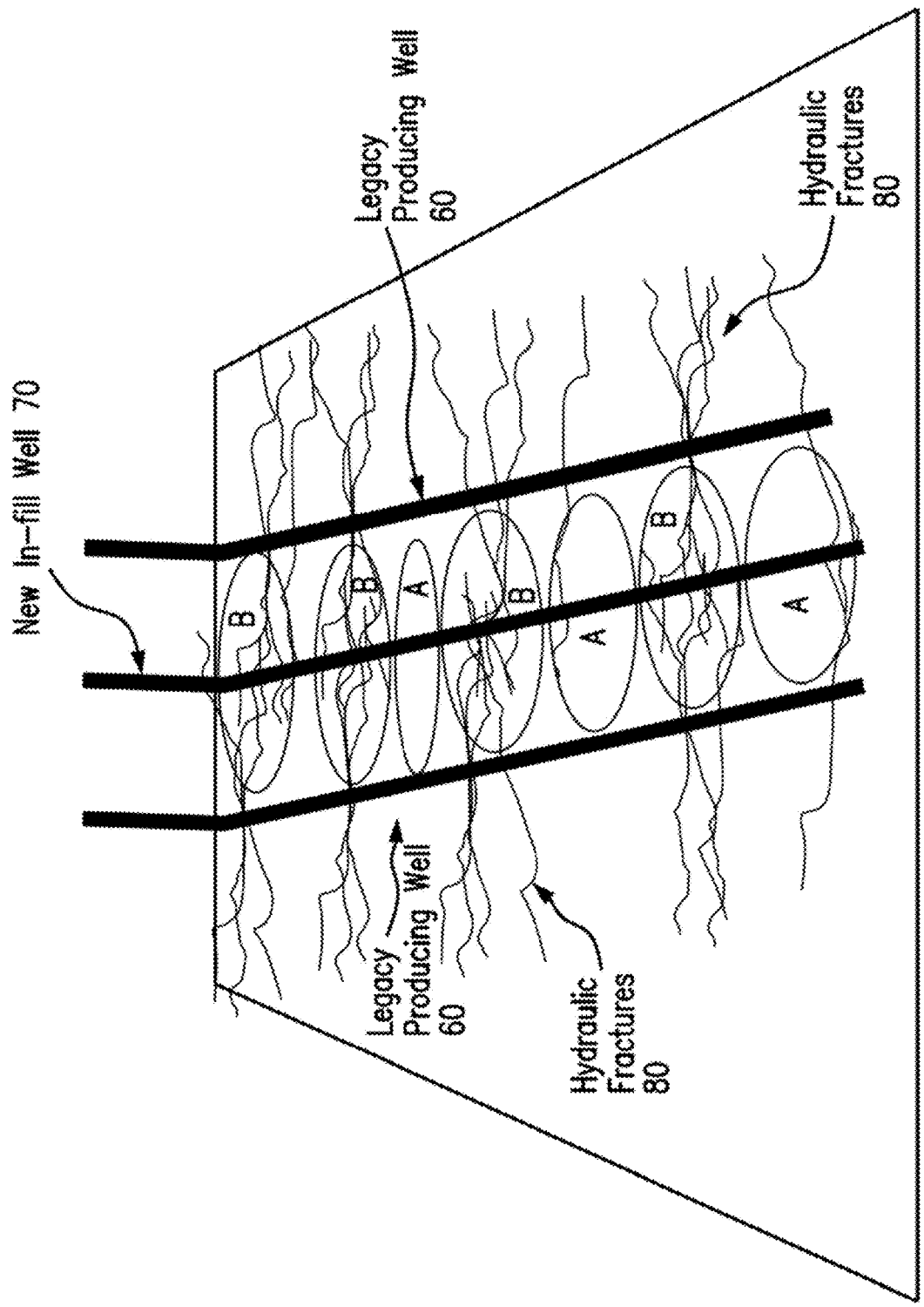
FIG. 14 shows a schematic of an in-fill well between two existing producing wells according to one preferred embodiment of the invention.

The in-fill well 70 is typically drilled mid-way between two pre-existing producing wells as shown in FIG. 14. The in-fill well 70 traverses the reservoir, which contains pre-existing fractures 80 emanating from the two offset producing, or legacy, wells 60.

Figure 15:
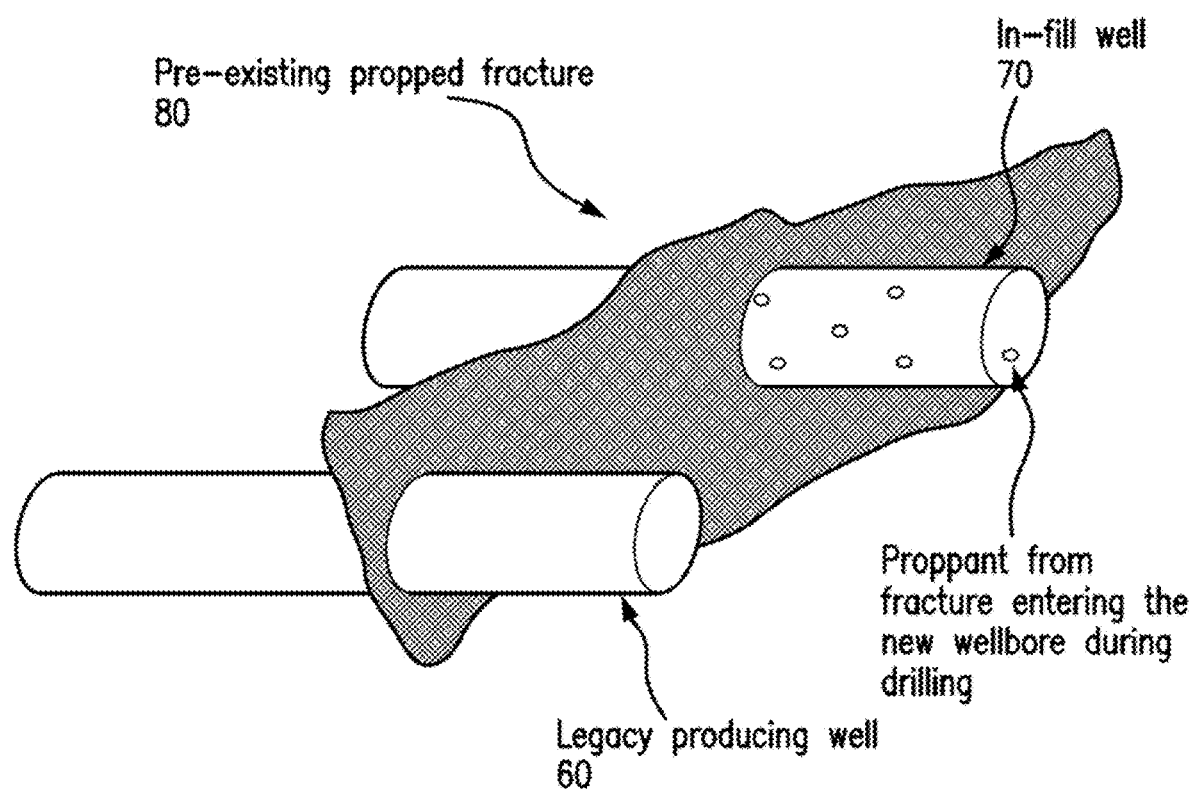
FIG. 15 shows a schematic of an intersection between an in-fill well and a propped hydraulic fracture according to one preferred embodiment of the invention.

As the in-fill well 70 is drilled between two pre-existing producing wells 60 that have been fracture stimulated, the new borehole crosses previously created hydraulic fractures which may or may not contain proppant. When proppant is encountered during drilling, it mixes with the drilling mud and the rock cuttings and is conveyed to the surface via the drilling mud as shown in FIG. 15. The return drilling mud at the surface containing the proppant can be sampled and the proppant distribution can be determined. Proppant can be similarly sampled in a new well which flanks a preexisting well.

Detecting Proppant On-The-Fly

Our prior work has shown that proppant can be detected and quantified from drilling mud sludge by first washing the sludge sample, then sieving the sample between two or more screens that are outside of the minimum and maximum range of the proppant size. The remaining sieved sample containing the proppant and rock cuttings is then placed under a camera or on a flatbed scanner in order to identify and quantify the proppant grains. This technique can be replicated at the rig site by collecting the drilling sludge from the shale shakers and various mud filters supporting the rig. The collected sludge samples can be analyzed on location or sent to an offsite lab.

Figure 16:
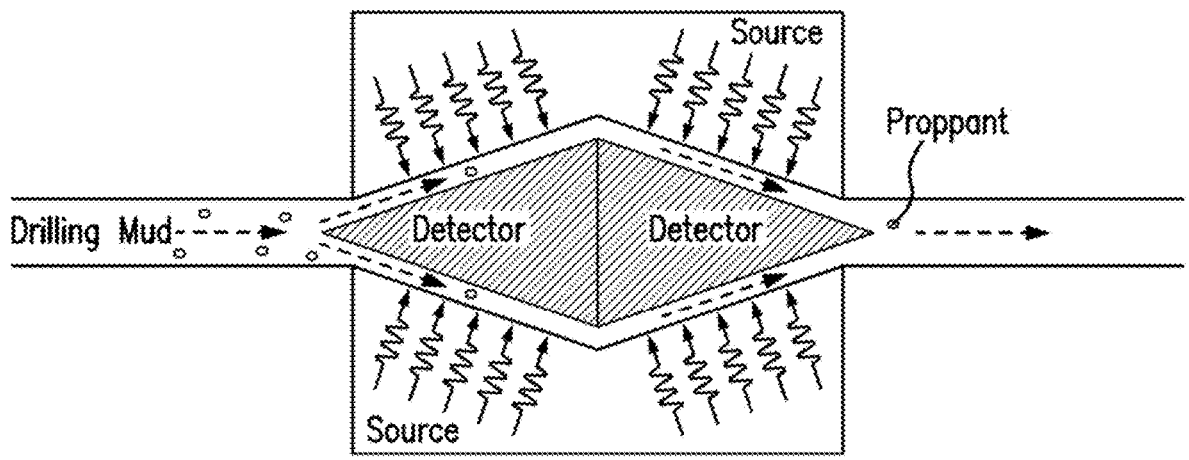
FIG. 16 shows a schematic of an instrument for detecting proppant in drilling mud in realtime according to one preferred embodiment of the invention.
Figure 17:
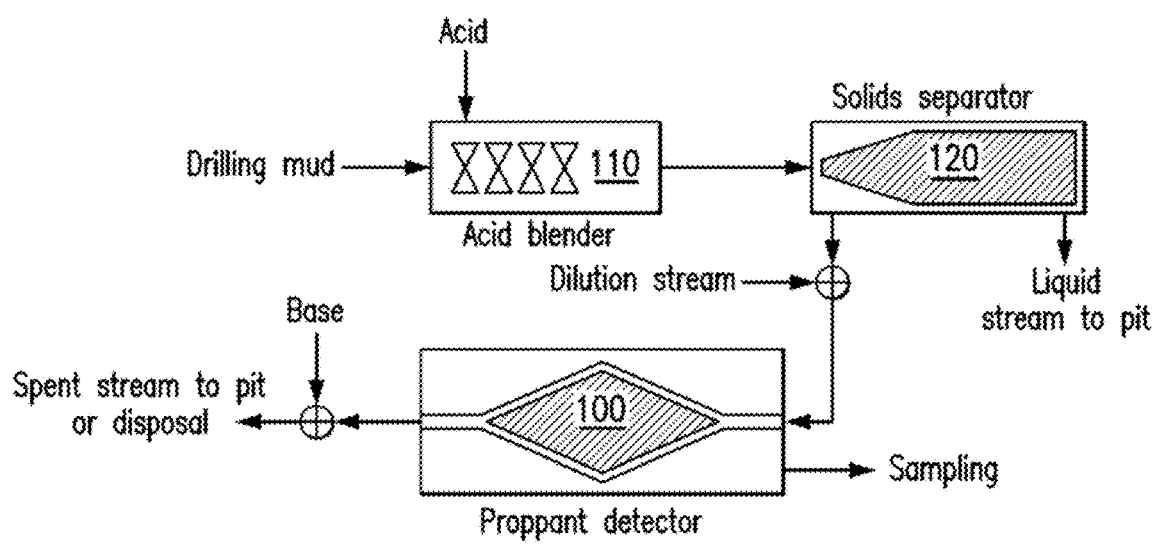
FIG. 17 shows a schematic of an instrument for detecting proppant according to one preferred embodiment of the invention.

While this technique works well, it may be inefficient considering large number of sampling requirements while drilling a horizontal well lateral extending thousands of feet. Another approach includes a method where proppant can be quantified in real time, i.e., on the fly during drilling of the in-fill well. This method would utilize either the full volume of the mud return stream, or a partial, split stream. The mud would then flow through an instrument that would detect the volume of the proppant in the stream as shown in FIG. 16. The instrument could have an energy source and receiver arrays for detecting the proppant, called a detector 100 herein. This could include various forms of electromagnetic radiation as well as nuclear energy, and basic particles of matter, such as protons, electrons, fermions, etc. In addition, imaging methods utilizing imaging under white, IR and UV lights, etc. can also be implemented. In order to reduce the cross section of the flow stream, and/or the flow velocity, the detector 100 could utilize a cone shape or a ramp insert. The reduced cross section and reduced stream velocity would allow the instrument to better detect proppant by reducing the volume/detector of fluid being sampled at any given time. An example of such a workflow utilizing real time proppant detection is shown in FIG. 17.

For improved performance, the fluid stream may be pretreated with a strong acid or a base, for instance, in a blender 110, to dissolve much of the clay and other material within the flow stream but retain proppant particles. To remove the oily matter, a suitable solvent such as methanol could also be used through the blender 110. Along with such treatment, a solids separator 120, such as a centrifuge or system such as a centrifuge cascade may be used to filter most of the light particles and only allow the weight fractions of interest to move on to the detector 100. These systems and units will have to be maintained at elevated temperatures depending on the residence time of a sample within these units, unit volume, and other relevant factors needed for the chemical reactions to be defined based on the treatment fluids to be used. Such separation mechanism can also be used to reduce the feed stream size going into the instrumentation and thereby allow more time for analysis and real time implementation of the system. In order to benchmark the drilling fluid itself to make sure that false positives are avoided where possible, the fluid from the pit or mixing tanks should be tested through the instrumentation before actual use. For further benchmarking, drilling mud returns from drilling of overlaying formations should also be tested through the instrumentation (i.e., before samples start returning material from the formation of interest).

Figure 18:
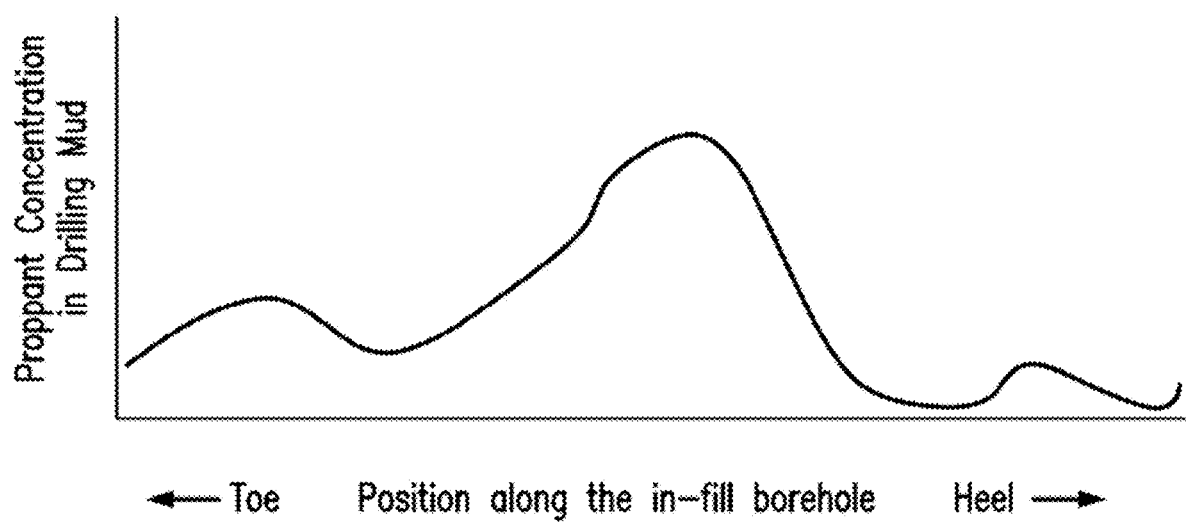
FIG. 18 shows a chart of data collected from a proppant measuring instrument according to one preferred embodiment of the invention.

Other methods of quantifying the proppant in the drilling mud can be implemented. Data collected from the proppant measuring instrument would show the amount of proppant encountered in the subsurface along the path of the in-fill well. FIG. 18 shows an example of the proppant concentration with respect to the position of the in-fill well.

In-Fill Well Fracture Design and Spacing

The in-fill well can cross many fractures, however if little or no proppant is encountered in these fractures, they are likely not productive. In any case, a propped fracture is most likely to contribute to production and drain the surrounding reservoir. The amount of proppant detected in the drilling mud provides insight into the quantity of propped fractures being drilled through. The ultimate purpose of the in-fill well is to recover hydrocarbon reserves left behind by the original producing wells. This is best done by stimulating the parts of the reservoir which have been left unstimulated by the original hydraulic fracturing. By knowing the amount of proppant along the in in-fill or new flank well, we can deduce which parts of the reservoir have been unstimulated or poorly stimulated, and thus focus on these areas.

Figure 19:
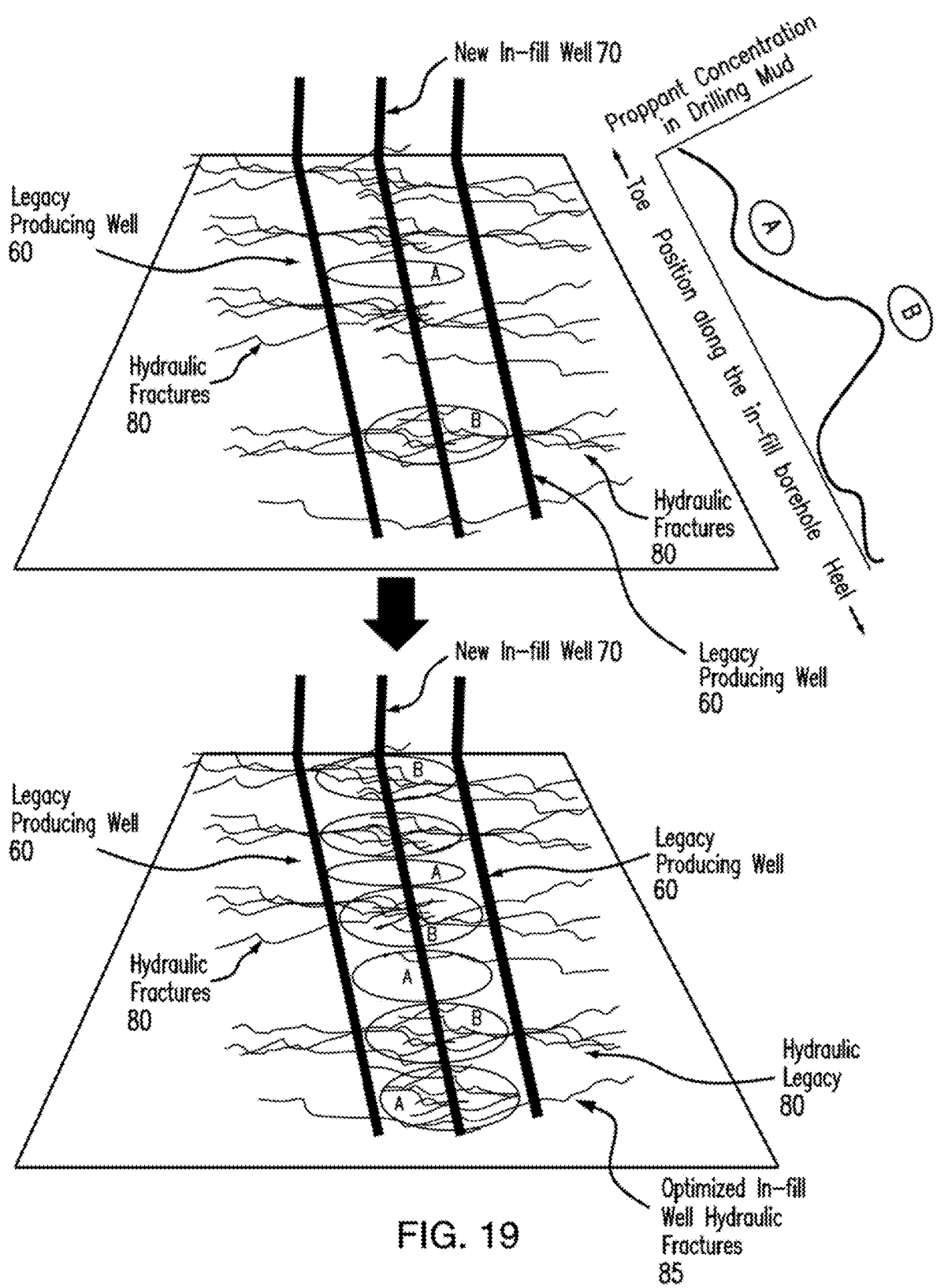
FIG. 19 shows a schematic of design and placement of hydraulic fractures in an in-fill well based on detected proppant distribution according to one preferred embodiment of the invention.

Typical stimulation of an in-fill well 70 would involve multiple fracture stages that are equally spaced and all having the same mass and volume of proppant and fluid, or what is called a geometric design. We utilize the proppant distribution data along the path of the in-fill well 70 to create an engineered fracture design. In the engineered fracture design, the fracture spacing would be based on the location and concentration of detected proppant. In the areas where little or no proppant was encountered, such as shown in FIG. 19, as shown in shaded areas A, the fracture spacing would be reduced and proppant and fluid volume would be increased. In these areas, we would expect optimized hydraulic fractures 85 resulting from the in-fill well 70. In areas of the reservoir where proppant concentration was high, as shown in shaded areas B in FIG. 19, the fracture spacing could be increased and proppant and fluid volume reduced, or new fractures could be eliminated altogether.

Utilizing Known Proppant Distribution for New Well Spacing and Stimulation

Understanding of proppant distribution in in-fill wells can be used to optimize the fracture design and spacing of new wells during field development to reduce the number of future in-fill wells. By drilling an in-fill well and finding the proppant concentration along the entire lateral, one can infer the effectiveness of the prior fracturing attempts. If too many fractures are encountered in the in-fill well then the well spacing in the offset wells is too close or the individual fracture stages are too large in volume. If few and far-between fracture stages are encountered, then the opposite is true. Furthermore, the fracture stages, or perforation clusters may need to be closer together to induce more fractures if few are noted.

For example, in one preferred model of the invention, if proppant is found to be, for example, 300 grains per foot of drilled wellbore, then the wells are too close since significant amounts of proppant were encountered, and a new increased well spacing of x feet may be proposed, or optimally, proppant concentration encountered is no higher than 50 grains per foot of drilled wellbore. If proppant concentration is found to be less than 50 grains per foot, the wells are too far apart, suggesting a reduced well spacing or increased fracture treatment size. Such proppant measurements may accordingly be used to determine position, suitability and spacing of in-fill or adjacent wells.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A method for optimized fracture treatment design in wells, the method comprising:
    isolating samples from drilling fluids to obtain a drilling fluids sample;
    analyzing the drilling fluids sample to isolate proppant using transparency scanning;
    determining whether a formation within the well has been stimulated based on the analysis; and
    planning the placement of an in-fill well based upon the determination of whether the well has been stimulated.

2. The method of claim 1 wherein the isolating step comprises washing and drying the drilling fluids sample and placing the sample on a high-resolution transparency scanner.

3. The method of claim 2 wherein the analyzing step comprises counting and sizing proppant in the drilling fluids sample.

4. The method of claim 2 wherein the analyzing step further comprises isolating shapes of interest within a scanning surface of the scanner.

5. The method of claim 4 wherein the shapes of interest are determined by measuring lightness of an edge of an object.

6. The method of claim 2 wherein the analyzing step further comprises determining an entropy of an object relative to a scanning surface of the scanner.

7. The method of claim 2 wherein the analyzing step further comprises determining an object color relative to a scanning surface of the scanner.

8. The method of claim 1 wherein the analyzing step comprises collecting attribute data of the proppant and performing qualitative and quantitative proppant analysis.

9. The method of claim 1 wherein the analyzing step includes comparing one or more attributes of the drilling fluids sample including color, hue, darkness, translucence and entropy against a transparent background.

10. The method of claim 1 wherein an excess of proppant relative to a previously measured amount of proppant determines whether stimulation of the formation is complete.

11. The method of claim 1 wherein the proppant is analyzed in real time as drilling fluids are removed from the formation.

12. The method of claim 1 wherein calcite particles are additionally analyzed.

13. A method for direct detection and quantification of proppant and other particles for optimized fracture treatment design in wells, the system comprising:
    channeling at least a portion of return drilling fluid through a particle detection device;
    detecting the proppant using transparency scanning;
    analyzing the proppant; and
    determining whether the formation has been fully stimulated based on the analysis.

14. The method of claim 13 wherein the channeling step comprises:
    channeling at least a portion of the drilling fluid return through a system of mixing and separation units;
    dissolving and removing oil and clay;
    retaining the proppant in a clean stream; and
    moving the cleaned stream into a detection unit.

15. The method of claim 14 wherein the analyzing step further comprises using a particle detector to identify presence of radioactive proppant in the channel stream.

16. The method of claim 15 wherein the particle detector comprises one of an alpha, beta and gamma particle detector.

17. The method of claim 14 wherein the analyzing step further comprises using an electromagnetic detector to identify presence of magnetic proppant particles.

18. The method in claim 13 wherein the analyzing step further comprises using a wavelength range including at least one of Ultraviolet, Infrared or visible radiation spectrum to illuminate and image the channel stream and image sensors to capture the illuminated stream.

* * * * *